(12) United States Patent
Gupta et al.

(10) Patent No.: US 10,068,740 B2
(45) Date of Patent: Sep. 4, 2018

(54) DISTRIBUTED, FIELD EMISSION-BASED X-RAY SOURCE FOR PHASE CONTRAST IMAGING

(71) Applicants: The General Hospital Corporation, Boston, MA (US); Massachusetts Institute of Technology, Cambridge, MA (US)

(72) Inventors: Rajiv Gupta, Wayland, MA (US); Luis Fernando Velasquez-Garcia, Cambridge, MA (US); Richard Lanza, Cambridge, MA (US); Berthold K P Horn, Boston, MA (US); Akintunde Ibitayo Akinwande, Cambridge, MA (US)

(73) Assignees: The General Hospital Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 307 days.

(21) Appl. No.: 14/400,836

(22) PCT Filed: Mar. 14, 2013

(86) PCT No.: PCT/US2013/031553
§ 371 (c)(1),
(2) Date: Nov. 13, 2014

(87) PCT Pub. No.: WO2013/184213
PCT Pub. Date: Dec. 12, 2013

(65) Prior Publication Data
US 2015/0124934 A1    May 7, 2015

Related U.S. Application Data

(60) Provisional application No. 61/646,577, filed on May 14, 2012.

(51) Int. Cl.
*A61B 6/00* (2006.01)
*A61B 6/03* (2006.01)
(Continued)

(52) U.S. Cl.
CPC ............ *H01J 35/065* (2013.01); *A61B 6/032* (2013.01); *A61B 6/40* (2013.01); *A61B 6/405* (2013.01);
(Continued)

(58) Field of Classification Search
CPC ......... A61B 6/032; A61B 6/40; A61B 6/4007; A61B 6/405; A61B 6/484; H01J 35/025;
(Continued)

(56) References Cited

U.S. PATENT DOCUMENTS 4,670,894 A * 6/1987 Birnbach ................. G21K 1/02
378/122
5,226,067 A * 7/1993 Allred ...................... G21K 1/10
378/140
(Continued)

FOREIGN PATENT DOCUMENTS

RU         2195739 C2    12/2002

OTHER PUBLICATIONS

L. F. Velásquez-Garcia, B. Adeoti, Y. Niu, and A. I. Akinwande, "Uniform High Current Field Emission of Electrons from Si and CNF FEAs Individually Controlled by Si Pillar Ungated FETs," 2007 IEEE International Electron Devices Meeting, Washington, DC, 2007, pp. 599-602.*
International Search Report and Written Opinioin dated Dec. 19, 2013 in connection with PCT/US2013/031553.

*Primary Examiner* — Allen C. Ho
(74) *Attorney, Agent, or Firm* — Quarles & Brady LLP

(57) ABSTRACT

An x-ray source for use in Phase Contrast Imaging is disclosed. In particular, the x-ray source includes a cathode array of individually controlled field-emission electron guns.

(Continued)

The field emission guns include very small diameter tips capable of producing a narrow beam of electrons. Beams emitted from the cathode array are accelerated through an acceleration cavity and are directed to a transmission type anode, impinging on the anode to create a small spot size, typically less than five micrometers. The individually controllable electron guns can be selectively activated in patterns, which can be advantageously used in Phase Contrast Imaging.

5 Claims, 4 Drawing Sheets

(51) Int. Cl.
| | |
|---|---|
| H01J 35/06 | (2006.01) |
| H01J 35/08 | (2006.01) |
| H01J 35/12 | (2006.01) |
| G01V 5/00 | (2006.01) |
| H01J 35/04 | (2006.01) |
| H01J 35/02 | (2006.01) |
| H01J 35/14 | (2006.01) |
| H01J 35/18 | (2006.01) |
| G01N 23/04 | (2018.01) |

(52) U.S. Cl.
CPC .......... *A61B 6/4007* (2013.01); *A61B 6/4405* (2013.01); *A61B 6/484* (2013.01); *G01N 23/04* (2013.01); *G01V 5/0016* (2013.01); *G01V 5/0041* (2013.01); *H01J 35/025* (2013.01); *H01J 35/04* (2013.01); *H01J 35/045* (2013.01); *H01J 35/12* (2013.01); *H01J 35/14* (2013.01); *H01J 35/18* (2013.01); *G21K 2207/005* (2013.01); *H01J 2201/30449* (2013.01); *H01J 2235/062* (2013.01); *H01J 2235/068* (2013.01); *H01J 2235/087* (2013.01); *H01J 2235/186* (2013.01)

(58) Field of Classification Search
CPC ........ H01J 35/04; H01J 35/045; H01J 35/065; H01J 35/14; H01J 35/18; H01J 35/06; H01J 35/12
USPC ................ 378/2, 16, 36, 122, 137, 138, 161
See application file for complete search history.

(56) References Cited

U.S. PATENT DOCUMENTS

| | | | | | |
|---|---|---|---|---|---|
| 5,801,486 | A * | 9/1998 | Johnson | ................ | H01J 21/105 313/309 |
| 6,010,918 | A * | 1/2000 | Marino | .................. | H01J 3/022 313/293 |
| 6,015,323 | A * | 1/2000 | Moradi | .................... | H01J 9/025 445/24 |
| 6,031,250 | A * | 2/2000 | Brandes | ................ | H01J 1/3042 257/77 |
| 6,233,309 | B1 * | 5/2001 | Baptist | ................ | G03B 42/047 378/162 |
| 6,259,765 | B1 * | 7/2001 | Baptist | ................ | H01J 35/065 313/309 |
| 6,333,968 | B1 * | 12/2001 | Whitlock | ............. | B82Y 10/00 378/122 |
| 6,369,498 | B1 | 4/2002 | Skupien | | |
| 6,385,292 | B1 * | 5/2002 | Dunham | ................ | A61B 6/032 378/122 |
| 6,456,690 | B2 * | 9/2002 | Yamada | .................. | H01J 35/14 378/119 |
| 6,456,691 | B2 * | 9/2002 | Takahashi | ............. | B82Y 10/00 378/122 |
| 6,477,233 | B1 * | 11/2002 | Ribbing | ............... | A61N 5/1001 378/119 |
| 6,553,096 | B1 * | 4/2003 | Zhou | .................... | A61B 6/4488 378/122 |
| 6,661,876 | B2 * | 12/2003 | Turner | ................ | G01N 23/223 313/553 |
| 6,674,837 | B1 * | 1/2004 | Taskar | .................... | A61B 6/00 378/122 |
| 6,760,407 | B2 * | 7/2004 | Price | ....................... | H01J 35/24 378/119 |
| 6,791,278 | B2 * | 9/2004 | Russ | ...................... | H01J 3/021 313/307 |
| 6,806,630 | B2 * | 10/2004 | Birecki | .................. | B82Y 10/00 313/336 |
| 6,873,118 | B2 * | 3/2005 | Russ | ...................... | H01J 3/021 315/169.3 |
| 6,882,703 | B2 * | 4/2005 | Price | .................... | H01J 35/065 378/101 |
| 6,946,660 | B2 | 9/2005 | El-Hanany et al. | | |
| 6,980,627 | B2 * | 12/2005 | Qiu | ....................... | H01J 35/065 378/122 |
| 7,042,982 | B2 * | 5/2006 | Pau | .......................... | G21K 7/00 250/396 R |
| 7,065,174 | B2 * | 6/2006 | Sipila | .................. | G01N 23/223 378/44 |
| 7,082,182 | B2 * | 7/2006 | Zhou | ...................... | A61B 6/032 378/10 |
| 7,085,351 | B2 * | 8/2006 | Lu | ......................... | A61B 6/4021 315/169.3 |
| 7,192,031 | B2 * | 3/2007 | Dunham | ................ | A61B 6/032 378/122 |
| 7,197,116 | B2 * | 3/2007 | Dunham | ................ | H01J 35/10 378/124 |
| 7,428,298 | B2 * | 9/2008 | Bard | ...................... | H01J 35/14 378/119 |
| 7,453,981 | B2 * | 11/2008 | Baumann | ............ | A61B 6/484 378/21 |
| 7,505,562 | B2 * | 3/2009 | Dinca | .................. | G01N 23/201 378/57 |
| 7,526,068 | B2 * | 4/2009 | Dinsmore | ............... | H01J 35/06 378/121 |
| 7,627,087 | B2 * | 12/2009 | Zou | ......................... | H01J 1/304 378/122 |
| 7,801,277 | B2 * | 9/2010 | Zou | ...................... | H01J 35/065 378/119 |
| 7,809,114 | B2 * | 10/2010 | Zou | ....................... | H01J 1/3048 378/122 |
| 7,826,594 | B2 * | 11/2010 | Zou | ........................... | H01J 1/30 378/10 |
| 7,826,595 | B2 * | 11/2010 | Liu | ....................... | H01J 35/065 378/122 |
| 7,844,032 | B2 * | 11/2010 | Vermilyea | ............. | G21K 1/025 378/149 |
| 7,873,146 | B2 * | 1/2011 | Okunuki | .............. | H01J 35/065 378/122 |
| 7,889,838 | B2 * | 2/2011 | David | .................. | A61B 6/4233 378/36 |
| 7,903,788 | B2 * | 3/2011 | Moore | .................... | H01J 35/06 378/121 |
| 7,924,973 | B2 * | 4/2011 | Kottler | ................. | G01B 15/025 378/36 |
| 7,924,983 | B2 * | 4/2011 | Moore | ...................... | H01J 35/06 378/122 |
| 7,976,218 | B2 * | 7/2011 | Vermilyea | ............. | G21K 1/025 378/124 |
| 7,978,816 | B2 * | 7/2011 | Matsuura | ............. | A61B 6/032 378/62 |
| 7,991,114 | B2 * | 8/2011 | Okunuki | .............. | A61B 6/032 378/11 |
| 7,991,120 | B2 * | 8/2011 | Okunuki | .................. | A61B 6/00 378/122 |
| 8,155,273 | B2 * | 4/2012 | Eaton | ................... | H01J 35/065 378/122 |
| 8,184,771 | B2 * | 5/2012 | Murakoshi | ....... | G01N 23/20075 378/145 |

(56) References Cited

U.S. PATENT DOCUMENTS

| | | | | |
|---|---|---|---|---|
| 8,198,106 B2 * | 6/2012 | Akinwande | H01J 1/3042 | 257/10 |
| 8,220,993 B2 * | 7/2012 | Takahashi | H01J 35/06 | 378/207 |
| 8,306,184 B2 * | 11/2012 | Chang | A61N 5/103 | 378/62 |
| 8,374,315 B2 * | 2/2013 | Freudenberger | H01J 35/06 | 378/134 |
| 8,385,506 B2 * | 2/2013 | Lemaitre | H01J 1/20 | 378/136 |
| 8,396,185 B2 * | 3/2013 | Zou | A61B 6/032 | 378/136 |
| 8,447,013 B2 * | 5/2013 | Sprenger | H01J 35/04 | 378/122 |
| 8,472,586 B2 * | 6/2013 | Ueda | H01J 35/065 | 378/121 |
| 8,477,908 B2 * | 7/2013 | Zou | H01J 35/065 | 378/136 |
| 8,488,742 B2 * | 7/2013 | Tsujii | A61B 6/4441 | 378/138 |
| 8,588,372 B2 * | 11/2013 | Zou | H01J 35/065 | 378/113 |
| 8,594,272 B2 * | 11/2013 | Funk | A61B 6/032 | 378/10 |
| 8,774,351 B2 * | 7/2014 | Funk | A61B 6/032 | 378/62 |
| 8,938,049 B2 * | 1/2015 | Kim | H01J 3/021 | 313/417 |
| 8,938,050 B2 * | 1/2015 | Lemaitre | H01J 35/06 | 378/113 |
| 9,064,670 B2 * | 6/2015 | Kim | H01J 3/021 | |
| 9,214,311 B2 * | 12/2015 | Funk | A61B 6/4064 | |
| 9,390,881 B2 * | 7/2016 | Yun | G21K 1/06 | |
| 2004/0095868 A1 | 5/2004 | Birecki et al. | | |

* cited by examiner

DISTRIBUTED, FIELD EMISSION-BASED X-RAY SOURCE FOR PHASE CONTRAST IMAGING

CROSS-REFERENCE TO RELATED APPLICATIONS

This application represents the national stage entry of PCT International Application No. PCT/US2013/031553 filed Mar. 14, 2013, which claims the benefit of U.S. provisional Patent Application 61/646,577, filed on May 14, 2012, both of which are incorporated herein by reference for all purposes.

STATEMENT REGARDING FEDERALLY SPONSORED RESEARCH

This invention was made with government support under N666001-11-4204 awarded by the Defense Advanced Research Projects Agency. The government has certain rights in the invention.

BACKGROUND OF THE INVENTION

The field of the invention is X-ray sources and corresponding imaging methods and systems. More particularly, the invention relates to an X-ray source for use in Phase Contrast Imaging (PCI).

Conventional X-ray systems generate images by assessing the difference in absorption of X-rays. Because currently conventional X-ray imaging techniques, such as computed tomography (CT), have attenuation parameters that are very similar to those of soft tissue, these systems cannot adequately differentiate soft tissue types, such as the soft tissue components of the plaque, including fibrous cap and atheroma. Similarly, conventional CT is not effective to distinguish tumor and surrounding healthy tissues.

To overcome these limitations, phase contrast imaging (PCI) methods have been developed. PCI methods rely on the difference in the refractive index of the imaged material which causes a phase shift, resulting in increased imaging contrast. This change in contrast mechanism can produce 1000-fold improvement in contrast-to-noise ratio when imaging soft tissues, and is particularly effective when imaging weakly absorbing samples such as soft tissues.

Although PCI provides significant improvements, in order to achieve an appreciable phase contrast effect which enables visualization of low-Z materials, PCI methods require a spectrally narrow X-ray source with a high degree of spatial coherence, and that is also preferably tunable. In particular, a X-ray source producing a bean having a small focal spot size, typically less than five micrometers, is desirable.

Currently, however, there are significant challenges to achieving a sufficiently small focal spot for PCI applications. Although there is a large body of literature in X-ray sources that can be brought to bear on the challenge proposed by PCI, PCI has only been shown to be feasible using monoenergetic coherent sources such as beam lines from synchrotrons.

It is also desirable, however, that the X-ray source be compact, portable, and operable from a power supply such as a battery or an auxiliary power unit (APU), and synchrotrons do not meet this goal. Although systems have been proposed to reduce the size of the apparatus required for generating coherent X-ray photons (e.g., by Inverse Compton Scattering). Miniaturized synchrotron radiation sources using a radio frequency linear particle accelerator (RF LINAC), and electro-cyclotrons on a chip have also been proposed. Because of their large size, and low interaction cross-section between the particles involved (typically, relativistic electrons and laser photons), even these so called "compact sources," do not meet the size or energy efficiency criteria desirable for PCI.

The present disclosure addresses these and other issues.

SUMMARY OF THE INVENTION

The present invention overcomes the drawbacks of the prior methods by providing an x-ray source that is portable, and provides programmable patterns of x-ray sources that can be used in PCI imaging.

In one aspect the present invention provides an x-ray source comprising an array of field emission cathodes, a transmission-type anode, and an acceleration cavity positioned between the array of cathodes and the anode. A controller is coupled to each of the array of cathodes, the controller programmed to selectively activate the cathodes in the array of cathodes to produce an electron beam from each selected cathode, the electron beam being accelerated through the acceleration cavity by an applied voltage and impinging on the anode to produce an X-ray beam.

In another aspect, the X-ray source can include a housing enclosing the cathode, the anode, and the accelerator cavity. A battery can be provided for powering the device. The X-ray source can also include an electrode stack positioned between the cathode and the anode for focusing the beam.

In another aspect, the field emission cathodes can also each include a tip having a diameter less than twenty nanometers. Each emitter in the array of field emission cathodes can also include an inner electrode that extracts current and an outer electrode that collimates the beam produced by the cathode. The electron beam produced by a cathode in the cathode array impinges on a portion of the anode can be is less than 5 micrometers in diameter.

In another aspect of the invention, each emitter in the array of field emission cathodes is individually controlled by a vertical ungated field effect transistor that controls each emitter's current. The anode can be poly-metallic, and can be constructed of at least one of a Tungsten (W), copper (Cu), and Molybdenum material. The anode materials can be in a matrix.

In still another aspect of the invention, the X-ray source can include a heat sink for cooling the anode. The heat sink can be constructed of beryllium (Be) construction, and can be etched to include a plurality of channels.

In another aspect of the invention, cathode array for use in producing an X-ray beam is provided. The cathode array comprises a plurality of emitters, each controlled by an ungated field-effect transistor. Each emitter includes an inner extractor electrode corresponding for extracting current; and an outer focusing electrode for collimating an electron beam produced by the emitter.

In yet another aspect of the invention, an anode for use in an x-ray source is provided. The anode plate comprises at least one of a tungsten, copper, and Molybdenum material, and a heat sink comprised of a beryllium sheet coupled to the anode plate. The beryllium sheet is etched to include a channeled cooling structure. The anode plate can be a poly-metallic plate comprising two or more of a tungsten (W), copper (Cu), and Molybdenum (Mo) material, and can comprise a two-dimensional matrix, each segment of the matrix comprising an X-ray generating material, or a poly-metallic segment comprising two or more layers of a tungsten (W), copper (Cu), and Molybdenum (Mo) material. The channels are photochemically etched into the beryllium sheet.

These and other aspects will become apparent from the following description. In the description, reference is made to the accompanying drawings which form a part hereof, and in which there is shown a preferred embodiment of the invention. Such embodiment does not necessarily represent the full scope of the invention and reference is made therefore, to the claims herein for interpreting the scope of the invention.

DETAILED DESCRIPTION OF THE PREFERRED EMBODIMENT

Figure 1:
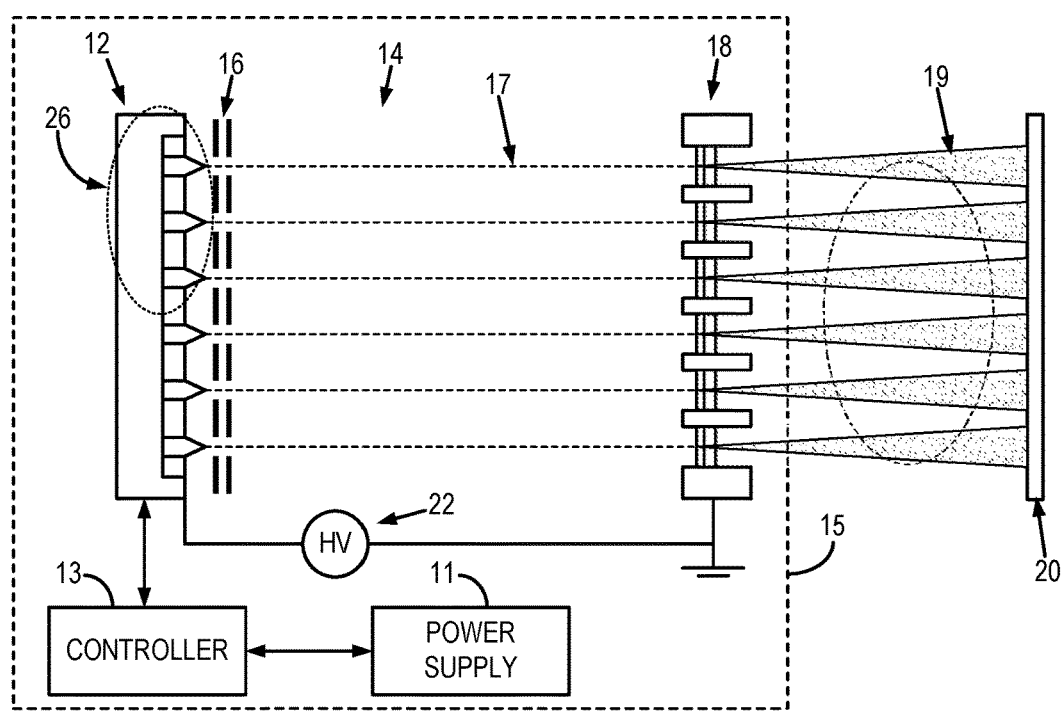
FIG. 1 is a schematic illustrating the components of an X-ray source constructed in accordance with the present disclosure, illustrated in use imaging an object.

Referring now to FIG. 1, an X-ray source 10 that can generate planar and tomographic images with conventional and phase-contrast imaging (PCI) methods is shown. The X-ray source 10 includes a distributed cathode array 12, an electron acceleration cavity 14, a lens 16, an anode 18, and an X-ray detector 20. A high voltage power supply 22 is coupled between the distributed cathode array 12 and the anode 18 to accelerate the electrons 17. A battery, auxiliary power unit, or other power supply 11 can be used as a power source for the system. X-ray beams 19 generated by the X-ray source 10 can be directed at an object or sample to be imaged, and an X-ray detector 20 can be positioned on the opposite side of the object to receive the X-ray beams 19. A controller 13, such as a microprocessor, microcontroller, or similar device with corresponding memory components and user interface can be connected to the distributed cathode array 12 and configured to selectively activate the cathodes in the distributed cathode array 12, as described more fully below.

The X-ray source 10 is preferably portable, and the components shown and described above can be located in a housing 15 with corresponding cables (not shown) to enable transportation of the device ray source 10. The housing 15 can enclose the distributed cathode array 12, the electron acceleration cavity 14, the anode 18, the power cables, and the cooling superstructure 42 discussed below. In the housing 15, the electron acceleration cavity 14 separates the distributed cathode array 12 from the anode 18, and can also house the lens 16 which focuses the electrons 17.

Referring still to FIG. 1, the lens 16 comprises an electrostatic lens that can be, for example, a micro-electrical mechanical system (MEMS) Einzel lens. The lens 16 focuses the electrons 17 produced by the distributed cathode array 12, and directs the electrons 17 to a small spot on the grounded anode 18. The lens 16 can be constructed of or coated with heavy metals capable of absorbing X-rays, which can protect the distributed cathode array 12 from backscatter.

Figure 2:
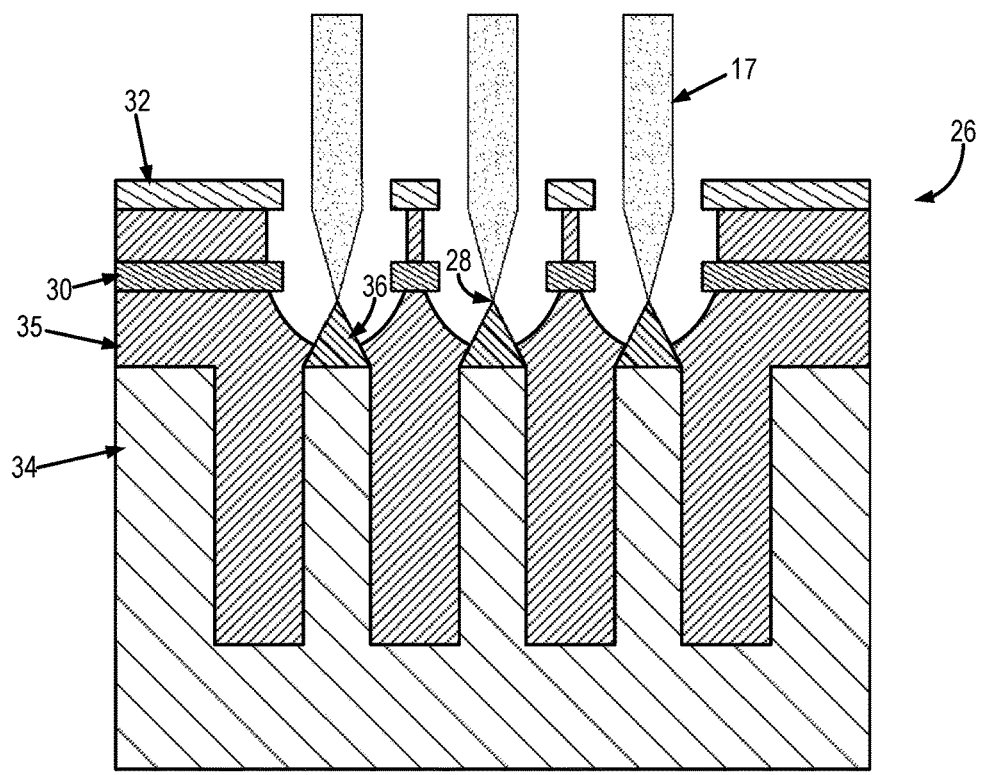
FIG. 2 is a cutaway view illustrating a cathode array used in the X-ray source of FIG. 1.
Figure 3:
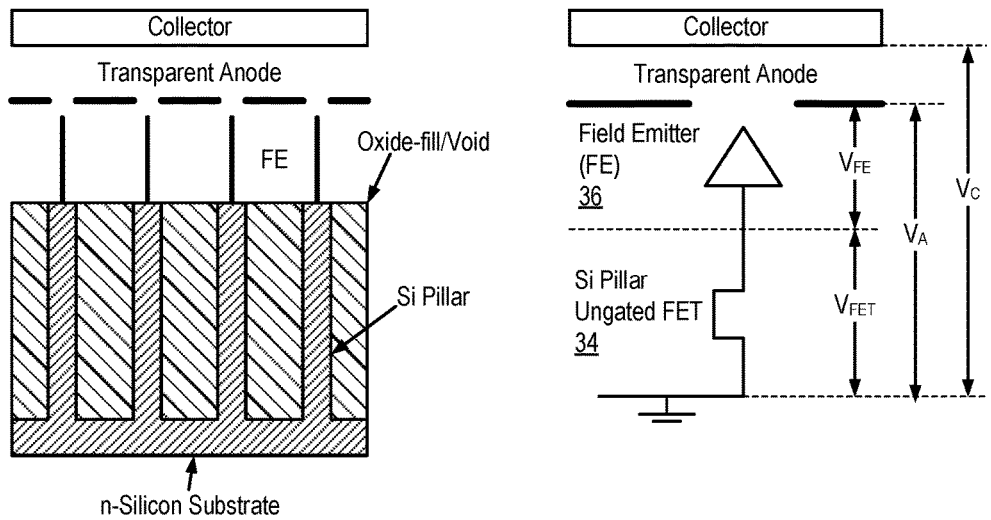
FIG. 3 is an alternate schematic illustrating the construction of the cathode array of FIG. 3.

Referring now to FIGS. 1-3, the distributed cathode array 12 comprises a matrix of field-emission electron guns which, in some applications, can be a hexagonal array to minimize gaps. Each of the field-emission electron guns includes a programmable gate and electrostatic lens 16. Referring now specifically to FIG. 2, the cathodes in the distributed cathode array 12 are composed of individually addressable X-ray elements (i.e., Xels) 26 for X-ray generation through Bremsstrahlung and line emissions, and can be multiplexed. The cathodes in the distributed cathode array 12 each include radiation-resistant ultra-sharp emitter tips 28 (~20 nm diameter) with near-mono-disperse tip radii distribution to provide uniform low operational voltage across the distributed cathode array 12. Uniform, high current can be produced by constructing the ultra-sharp emitter tips 28 of high work function materials. The distributed cathode array 12 can produce current densities between 1 and 10 milliamps per square centimeter.

Each Xel 26 can be composed of a plurality or small cluster of gated field emitters 36, resulting in a redundancy that increases Xel reliability. Each field emitter 36 includes two proximal self-aligned electrodes, including an inner extractor electrode 30 that achieves electron extraction at low voltage (mA-level current at ~100V), and an outer collimator electrode 32 that collimates the electrons 17. Each Xel 26 produces electrons 17 in a high-current electron beam and has an electrode stack that focuses the electrons 17 onto a small (<5 µm) spot size at the anode 18. Each field emitter 36 is individually controlled by a vertical ungated field effect transistor (FET) 34 that individually controls the current of each field emitter 36, equalizes the current across the distributed cathode array 12, and limits the maximum current per field emitter to avoid burn-out of the field emitters 36 (FIG. 2). Individual emitter ballasting also increases the cathode reliability by protecting it from electrical surges. The FETs 34 can also protect the field emitters 36 against burnout due to joule heating, and against current surges. In some embodiments, the FETs 34 can be hexagonal in cross-section to minimize gaps in the substrate. The outer collimator electrode 32 can also be coated with a heavy metal to protect the distributed cathode array 12 from backscatter. A dielectric material 35 is located between adjacent FETs 34.

Figure 4:
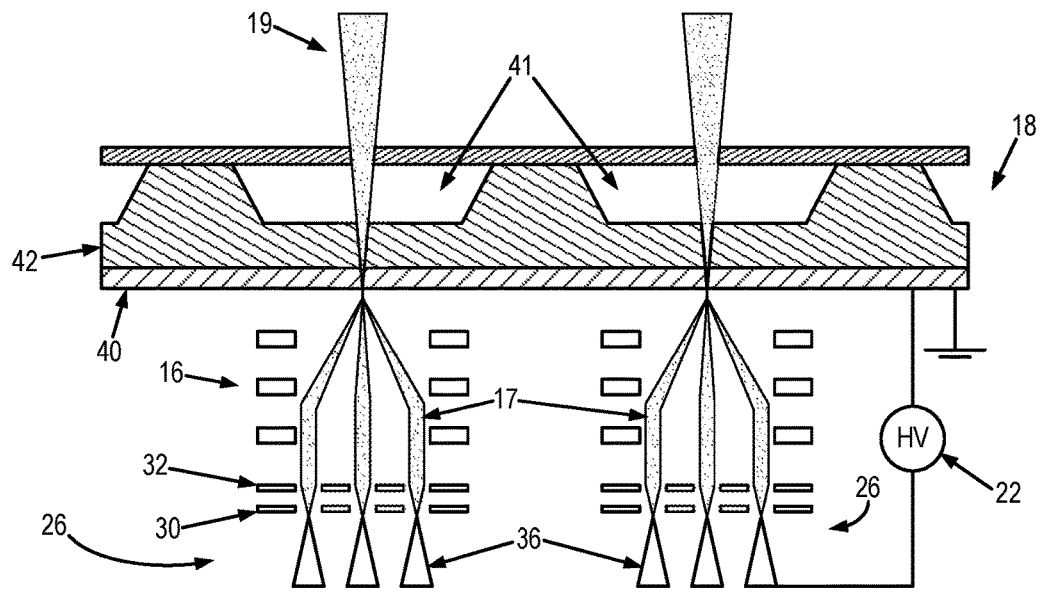
FIG. 4 is a schematic illustration of an anode and corresponding heat sink used in one embodiment of the X-ray source of FIG. 1.

Referring now to FIG. 4, as described above, the distributed cathode array 12 integrates vertical ungated FET 34 as individual feedback elements to control the emission current of each field emitter 36. In this architecture, each field emitter 36 is in series with a different high aspect ratio vertical ungated FET 34 that controls the supply of electrons available to each field emitter 36. When the bias voltage across the ungated FET 34 is larger than its saturation voltage, the ungated FET 34 acts as a current source (i.e., large current and large output resistance). The ungated FETs 34 will also increase the reliability of the distributed cathode array 12, as individual control of the supply of electrons available to each field emitter 36 limits the possibility of destructive emission from the ultra-sharp emitter tips 28 while allowing higher overall current emission because of the emission of duller tips. It has been shown experimentally that fully ballasted 0.5 A-level current emission from 1-million FEAs that span 1 square centimeter can be produced using the technology described here. In one application, deep reactive ion etching was used to form the columns. The columns were constructed at 25 μm tall, and 1.4 μm in diameter. Although an ungated FET 34 is described here, a diode, such as an n-p diode made on a p-Si substrate that provides flow control through velocity saturation operated in reverse bias mode, could also be used.

Referring again to FIG. 1, the electron acceleration cavity 14 separates the anode 18 from the distributed cathode array 12, and comprises a high-voltage power supply 22 that accelerates the electrons 17 before they impinge on the anode 18. The electron acceleration cavity 14 comprises a high-gradient electron acceleration cavity with $10^7$-$10^8$ V/m of electrostatic acceleration field over a 1-10 mm vacuum chamber between the distributed cathode array 12 and the anode 18, and electron flux through the electron acceleration cavity 14 is preferably in the range between about $10^{-4}$-$10^{-6}$ Torr. Electron acceleration is accomplished by accelerating the small quanta of electrons 17 (approximately 1 micro coulomb) by each field emitter 36 to between about 10 to 100 KeV. A conventional power supply capable of generating 10-100 kV voltage gradient may be employed. In one application, for example, the x-ray source 10 can use one or more commercial-off-the-shelf high-voltage power supply (e.g., Matsusada XPg-100N10 manufactured by Matsusada Precision, Inc., 745 Aojicho, Kusatsu, Shiga 525-0041 Japan) that can ground the anode 18, hold −100 kV on the distributed cathode array 12, and supply 10 mA of current.

Referring still to FIGS. 1 and 2, the anode 18 is preferably a transmission type anode. The electrons 17 from the field emitters 36 of the distributed cathode array 12 impinge on a first face of the anode 18 while the X-ray beams 19 exit the opposing face of the anode 18. Configuring the anode 18 as a transmission type anode provides advantages over other types of devices because X-ray flux from a transmission type anode has a higher ratio of K-line to continuum radiation and shows a more significant amount of energy in the K-line. The X-ray flux from a transmission type anode is thus more monochromatic, and more closely simulates a set of point sources. These properties make a transmission type anode more desirable for phase contrast imaging. When using a transmission type anode, the total dissipated power is also spread out over a much larger area than conventional X-ray tubes, minimizing heat concerns.

Referring now to FIG. 4, the arrangement of the anode 18 in front of the distributed cathode array 12 is shown schematically. As described above, the anode 18 includes a cooling structure 42 or manifold constructed of beryllium (Be). The cooling structure 42 is separate from the anode substrate 40 itself, and therefore, the complexity of the cooling structure 42 is de-coupled from the anode substrate 40. The cooling structure 42 can be designed to meet heat sink requirements up to 1000 W/cm². The heat sink requirements for the anode 18 can be determined for a particular application by estimating the thermal loading and designing an appropriate heat exchanger. The thickness of the X-ray emitting material, and the estimated and measured angular and spectral distribution of photon flux can be used to determine an appropriate level. Thermal problems can be managed by increasing the thermal mass using high-conductivity, low-Z materials and introducing cooling at or near the location of hot spots.

Referring again to FIGS. 1, 2, and FIG. 4, in one embodiment the anode 18 comprises a poly-metallic construction including a tungsten or copper anode substrate 40 with a beryllium (Be) cooling structure 42 or superstructure. The cooling structure 42 can include a micro-channel cooling system that can be constructed using thin Be sheets having thicknesses of about 25-50 micrometers, which can be photochemically etched with selected patterns to form channels 41, and then stacked, and diffusion bonded to create a solid structure perforated with microscopic passages. The diffusion bonding process can be provided with clean Be—Be surfaces, and with silver (Ag) inter-layers. The Be cooling structure 42 can be mechanically coupled to the anode substrate 40.

Figure 6:
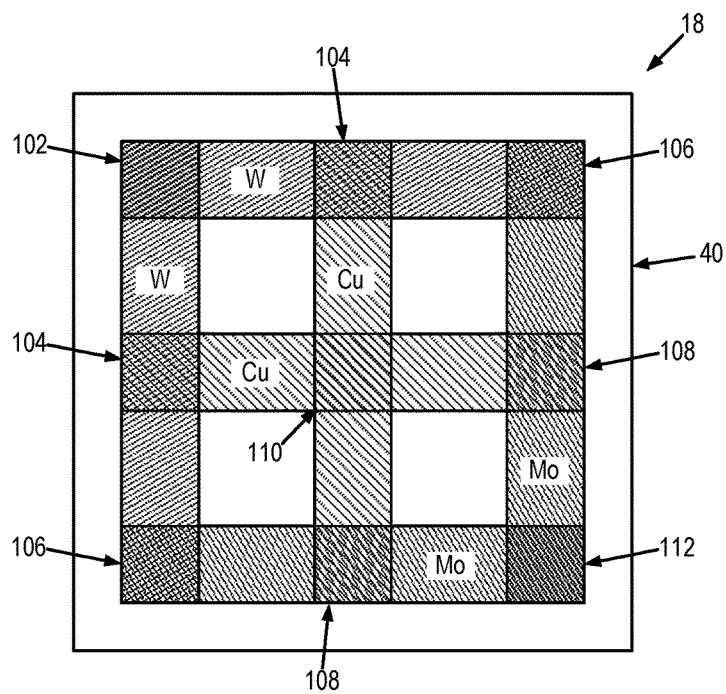
FIG. 6 is a schematic illustration of a poly-metallic anode plate.
Figure 5:
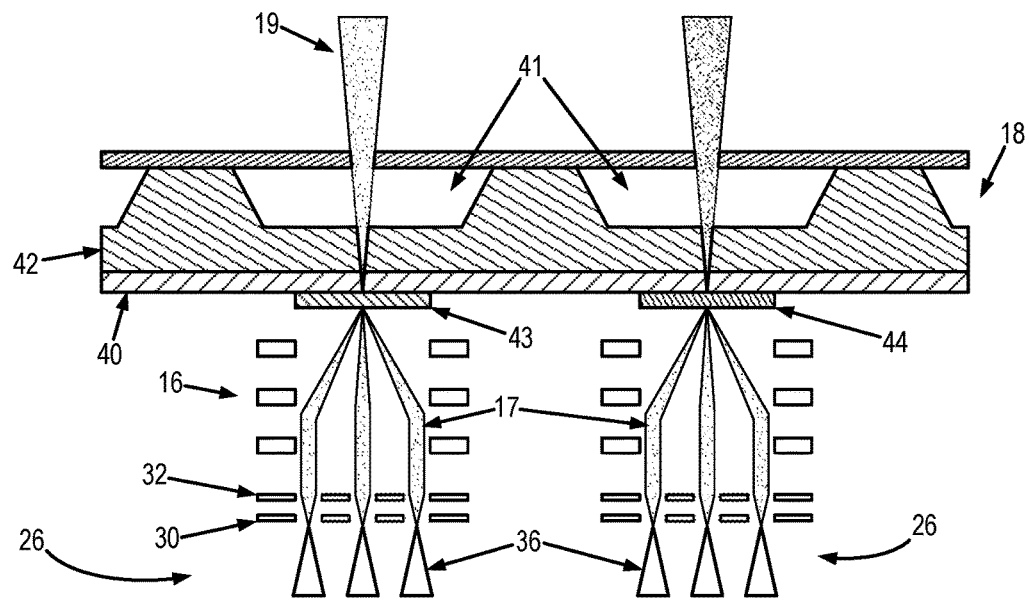
FIG. 5 is a is a schematic illustration of an anode and corresponding heat sink used in another embodiment of the X-ray source of FIG. 1.

Referring now to FIG. 5, an alternate embodiment is shown for use in applications, for example, where the anode 18 will face a more advanced distributed cathode array 12 with each Xel 26 capable of 8 mA or more of current and 100 kV operation. In these applications, the anode 18 can be constructed with a poly-metallic design with multiple layers of anode material, including additional poly-metallic layers 43, 44. Several arrangements of poly-metallic anode plate with respect to the electron guns can be provided. Here, the anode substrate 40 can comprise layers of Tungsten (W), copper (Cu), and Molybdenum (Mo). In one such arrangement, such as the one illustrated in FIG. 6, a 2D matrix of X-ray generating materials (Cu, Mo, W) can be provided. Portions of the array can include W—W portions 102, Cu—W portions 104, Mo—W portions 106, Cu—Mo portions 108, Cu—Cu portions 110, and Mo—Mo portions 112, by way of example. Other constructions, comprising, for example, a polymetallic anode, three metals and nine bimetal combinations can provide more advanced heat exchange properties.

The structure 42 is preferably constructed to be capable of removing the waste heat flux of up to 100 Watts per cubic centimeter while maintaining the anode 18 at less than 45° C. It has been shown experimentally that forced air cooling is typically adequate in PCI medical imaging applications where power dissipation is relatively low because of increase in the signal-to-noise and contrast-to noise ratios as compared to traditional imaging techniques. However, chilled fluids, such as water, may also be used, particularly for higher power applications such as pure attenuation-based imaging and for non-destructive evaluation.

As described above, the X-ray source 10 preferably includes a controller 13 adapted to activate and deactivate individual field emitters 36 in the distributed cathode array 12. The controller 13 enables multiplexed, programmable firing of the Xels 26 and enables use of the X-ray source 10 in coded source imaging for use in PCI. Although a dedicated controller 13 can be located within the housing 15 described above, in some applications the control circuitry can be provided by off-the-shelf electronics and system controllers such as the A500 and B10 from Pyramid Technological Consulting, Inc, Waltham, Mass.

Figure 7:
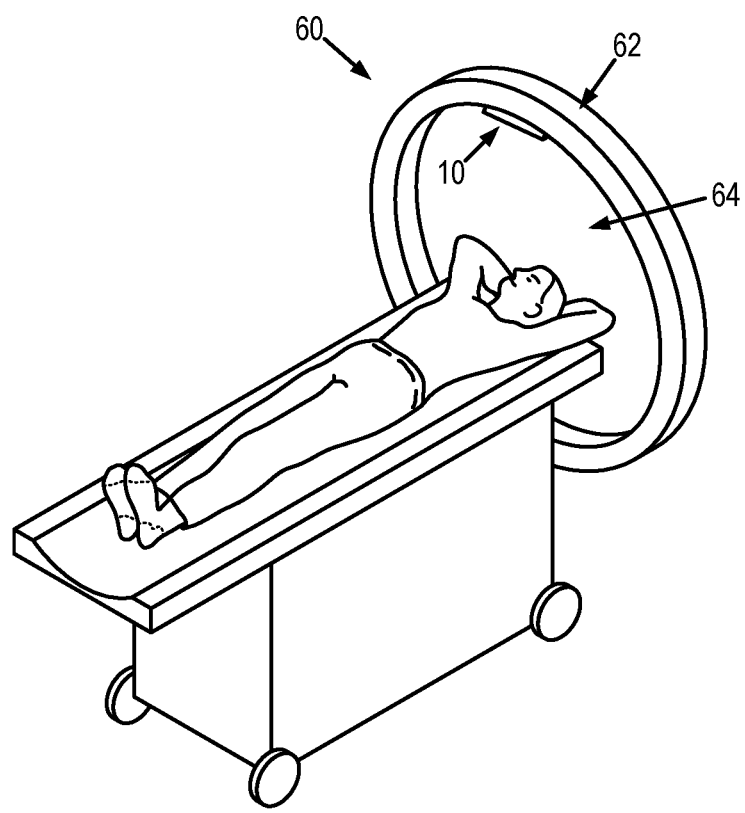
FIG. 7 is an illustration of a gantry for use with the X-ray source of FIG. 1.

Referring now to FIG. 7, the X-ray source 10 can be coupled to a gantry system 60. The gantry system 60 includes a generally circular frame structure 62 including an open central area 64 for receipt of an imaging patient. The X-ray source 10 and a corresponding X-ray detector can be coupled to the gantry system 60 and rotated along the circular frame structure 62 and about the patient for imaging. As shown here, the size and height of the open central area 64 can be selected to receive a patient transport device.

In operation, the controller 13 in the portable X-ray source 10 selectively activates each Xel 26 in the distributed cathode array 12 to produce a beam of electrons 17 which are accelerated through the electron acceleration cavity 14 to impinge on the anode 18 with a focal spot size ranging from sub-micron to about 5 micrometers. Phase contrast imaging can be provided using coded-source or coded aperture imaging techniques. As described above, PCI increases tissue contrast, reduces dose and requires a less powerful X-ray source so as to achieve comparable or better image quality, thus forming the basis for low-powered, fieldable imaging systems.

The distributed cathode array 12 provides discrete sources that are arranged geometrically and that can act as "coded sources." These coded sources can be used to generate images which exhibit phase contrast. In particular, or X-ray imaging, phase contrast approaches based on (spatially) coherent X-ray sources can be used to form images which are based on refraction rather than absorption contrast if source sizes are 5 µm or less.

Using the X-ray source 10 described above, imaging of a sample can be performed using multiple simultaneous coherent X-ray sources produced individually by the distributed cathode array 12 described above. The X-ray sources can be activated by the controller 13 in a predetermined encoded pattern to provide a "coded source." Because of the large number of sources, X-ray power is spread over many anodes and thus limitations on power due to material properties are significantly reduced as compared to prior art systems. The small source size also permits spatially coherent image formation. While coded images produced by the different sources are not mutually coherent, their detector radiances can be summed, with each of the contributions sensitive to phase variations resulting from differences in refractive index.

It should be apparent that many variations from the above preferred embodiment are possible without departing from the invention. To apprise the public of the scope of the invention, the following claims are made:

The invention claimed is:

1. An anode for use in an x-ray source, the anode comprising:
   an anode plate comprising at least one of a tungsten (W), copper (Cu), and molybdenum (Mo) material;
   a heat sink comprising a beryllium (Be) sheet coupled to the anode plate; and
   wherein the beryllium sheet is etched to include a channeled cooling structure.

2. The anode as recited in claim 1, wherein the anode plate comprises a poly-metallic plate comprising two or more of a tungsten (W), copper (Cu), and molybdenum (Mo) material.

3. The anode as recited in claim 1, wherein the anode plate comprises a two-dimensional matrix, each segment of the two-dimensional matrix comprising a poly-metallic segment comprising two or more layers of a tungsten (W), copper (Cu), and molybdenum (Mo) material.

4. The anode as recited in claim 1, wherein the channeled cooling structure comprises channels that are photochemically etched into the beryllium sheet.

5. The anode as recited in claim 1, wherein the anode plate comprises a matrix of X-ray generating materials.

* * * * *

UNITED STATES PATENT AND TRADEMARK OFFICE
CERTIFICATE OF CORRECTION

Page 1 of 1

PATENT NO. : 10,068,740 B2
APPLICATION NO. : 14/400836
DATED : September 4, 2018
INVENTOR(S) : Rajiv Gupta et al.

It is certified that error appears in the above-identified patent and that said Letters Patent is hereby corrected as shown below:

In the Specification

Column 4, Line 39, "emitter to" should be --emitter 36 to--.

Column 4, Line 51, "FET" should be --FETs--.

Column 6, Line 30, "The structure" should be --The cooling structure--.

Signed and Sealed this
Sixteenth Day of October, 2018

Andrei Iancu
*Director of the United States Patent and Trademark Office*